(12) United States Patent  
May et al.

(10) Patent No.: US 7,794,462 B2  
(45) Date of Patent: Sep. 14, 2010

(54) HANDPIECE CALIBRATION DEVICE

(75) Inventors: Justin J. May, Leesburg, IN (US); Adam M. Griner, Columbia City, IN (US); Raymond C. Parisi, Wakarusa, IN (US)

(73) Assignee: Zimmer Technology, Inc., Warsaw, IN (US)

( * ) Notice: Subject to any disclaimer, the term of this patent is extended or adjusted under 35 U.S.C. 154(b) by 418 days.

(21) Appl. No.: 11/687,763

(22) Filed: Mar. 19, 2007

(65) Prior Publication Data

US 2008/0234664 A1 Sep. 25, 2008

(51) Int. Cl.  
*A61B 17/00* (2006.01)

(52) U.S. Cl. .................. 606/79; 606/1; 30/286

(58) Field of Classification Search .......... 30/173, 30/263, 286; 600/594; 606/1, 79, 102, 167, 606/170–172, 178–180  
See application file for complete search history.

(56) References Cited

U.S. PATENT DOCUMENTS

| | | | | |
|---|---|---|---|---|
| 2,353,514 A | * | 7/1944 | Slater | 408/72 R |
| 5,486,180 A | * | 1/1996 | Dietz et al. | 606/87 |
| 5,499,984 A | * | 3/1996 | Steiner et al. | 606/80 |
| 5,720,749 A | * | 2/1998 | Rupp | 606/79 |
| 6,162,226 A | * | 12/2000 | DeCarlo et al. | 606/80 |
| 6,434,507 B1 | * | 8/2002 | Clayton et al. | 702/152 |
| 6,514,258 B1 | * | 2/2003 | Brown et al. | 606/80 |
| 6,554,838 B2 | * | 4/2003 | McGovern et al. | 606/87 |
| 7,641,655 B2 | * | 1/2010 | Shores et al. | 606/79 |
| 2003/0139669 A1 | * | 7/2003 | Montegrande | 600/426 |
| 2006/0293682 A1 | * | 12/2006 | Justin et al. | 606/88 |
| 2008/0234683 A1 | | 9/2008 | May | |

\* cited by examiner

*Primary Examiner*—Thomas C Barrett  
*Assistant Examiner*—Larry E Waggle, Jr.  
(74) *Attorney, Agent, or Firm*—Baker & Daniels LLP

(57) ABSTRACT

A calibration device for a milling instrument is provided. The calibration device may be a burr guard which may be attached to the milling instrument. The calibration device may calibrate the milling instrument to provide a predetermined depth of alteration to an anatomical structure.

9 Claims, 5 Drawing Sheets

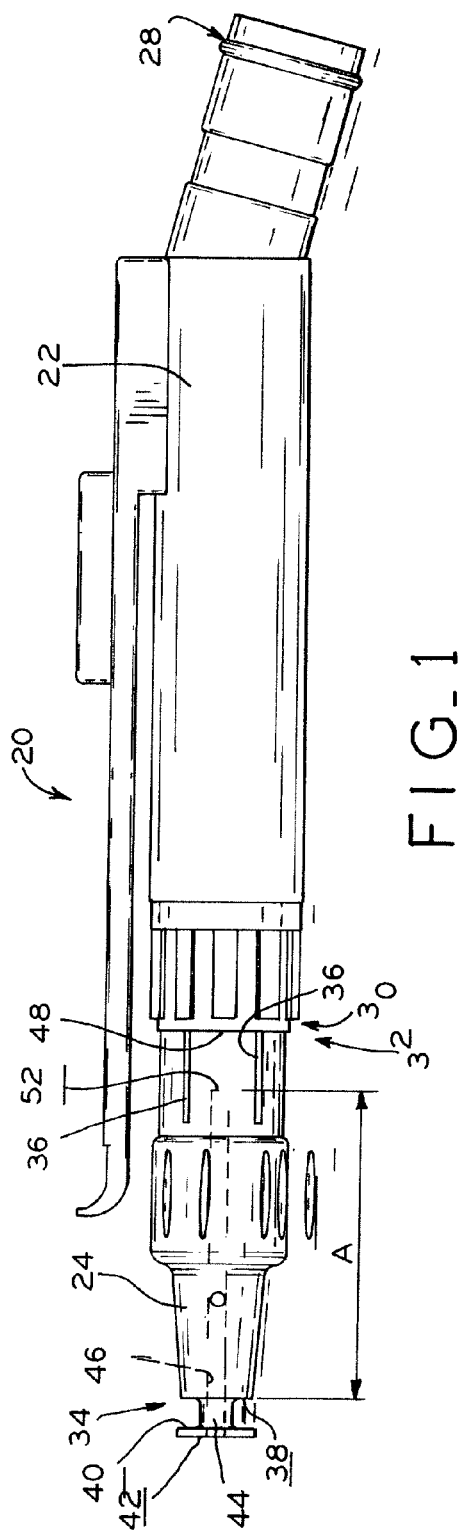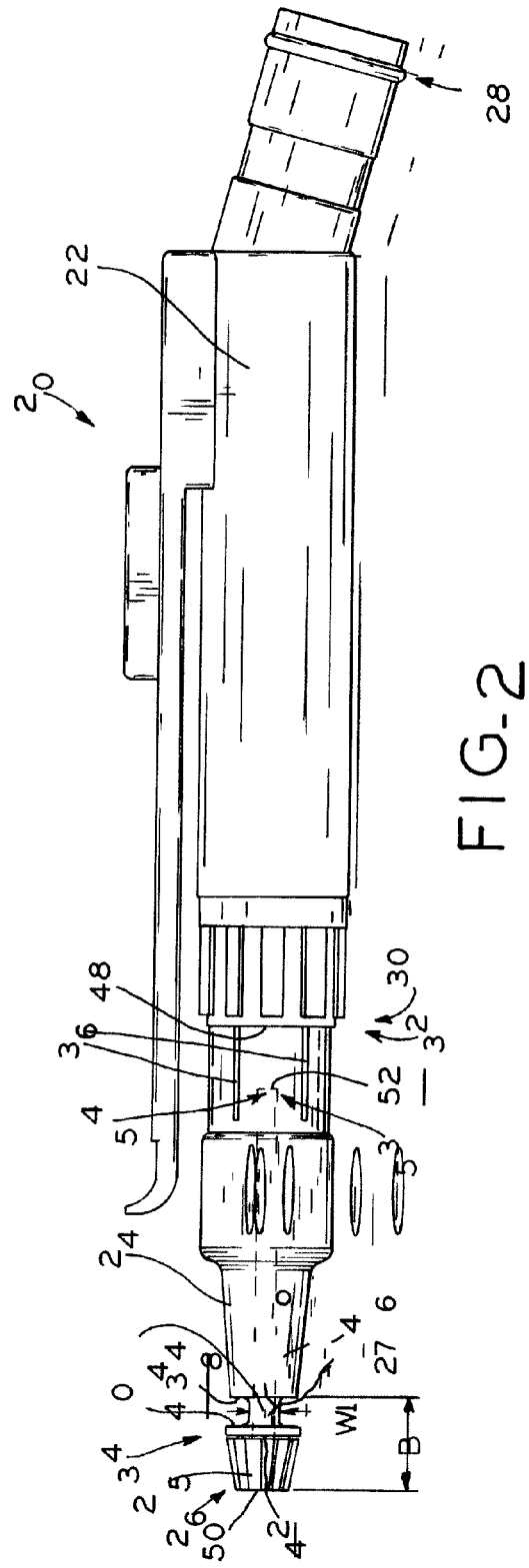

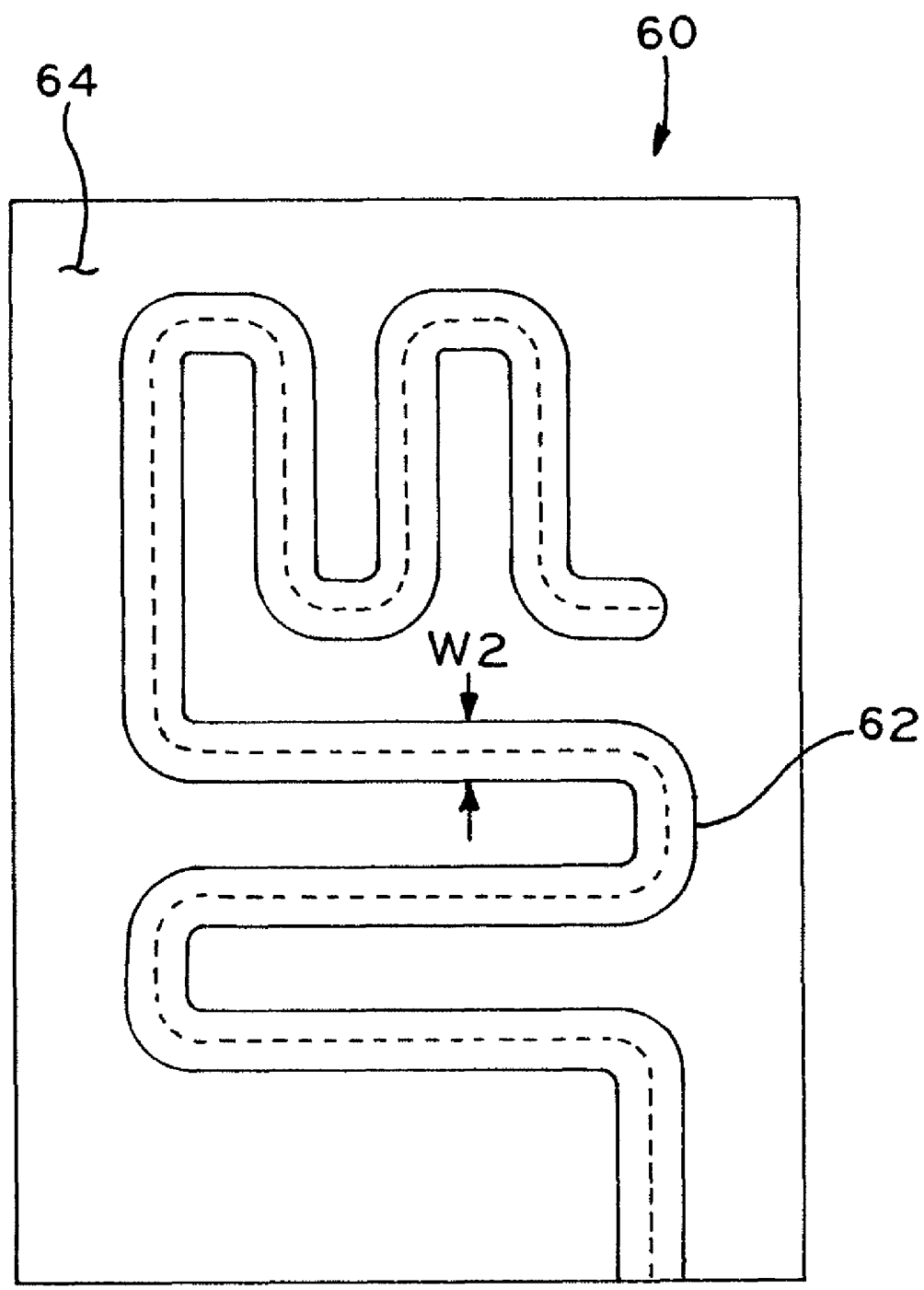
FIG_5

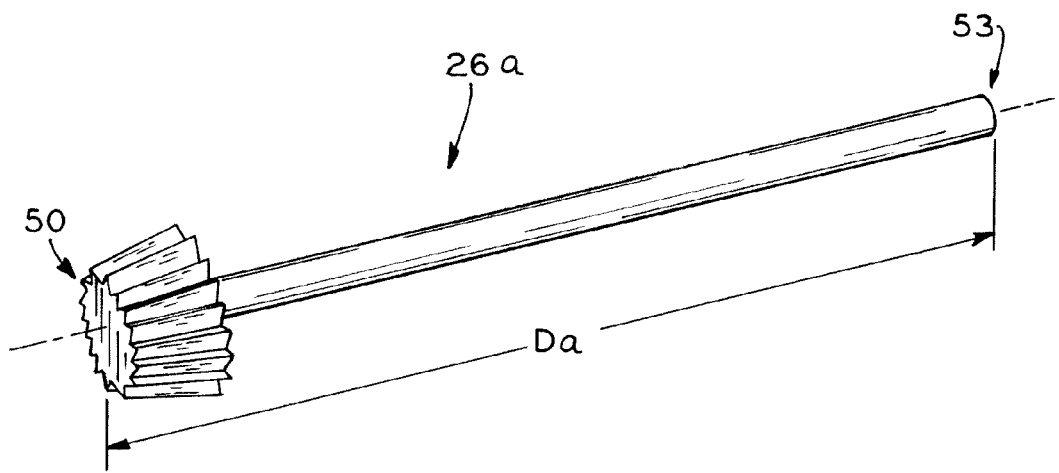
FIG_7A
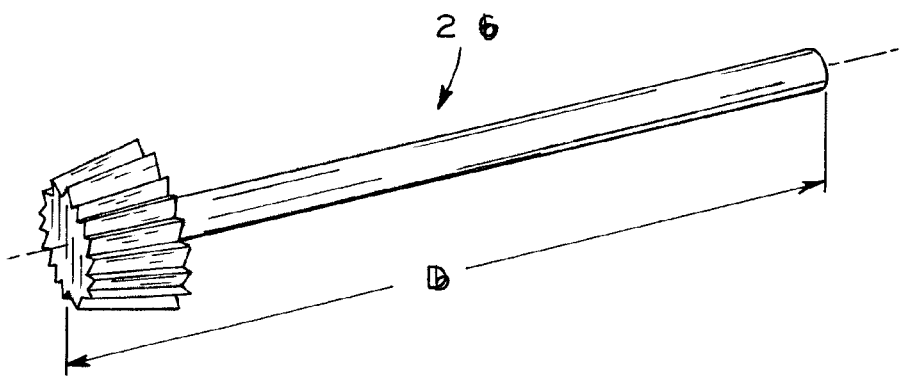
FIG_7B
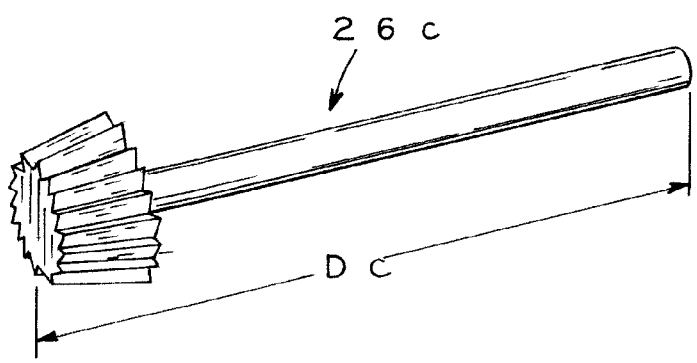
FIG_7C

HANDPIECE CALIBRATION DEVICE

BACKGROUND

1. Field of the Disclosure.

The present disclosure relates to an orthopaedic milling instrument. More particularly, the present disclosure relates to a calibration device for use with an orthopaedic milling instrument.

2. Description of the Related Art

A handpiece or handheld milling instrument may be used during an orthopaedic surgical procedure to remove portions of bones or other anatomical structures.

SUMMARY

The present disclosure provides a calibration device for a milling instrument. The calibration device may be a burr guard which may be attached to the milling instrument. The calibration device may calibrate the milling instrument to provide a predetermined depth of alteration to an anatomical structure.

In one form thereof, the present disclosure provides a system for use in altering an anatomical structure, the system including a surgical instrument; a plurality of alteration devices attachable to the surgical instrument; and a plurality of calibration devices attachable to the surgical instrument, each calibration device defining a predetermined depth of alteration for each alteration device.

In another form thereof, the present disclosure provides a system for use in altering an anatomical structure, the system including alteration means for altering the anatomical structure; and calibration means for calibrating a depth of alteration with the alteration means.

In yet another form thereof, the present disclosure provides a method for calibrating a surgical instrument, including the steps of providing a surgical instrument; attaching one of a plurality of calibration devices to the surgical instrument; attaching one of a plurality of alteration devices to the surgical instrument; and calibrating a depth of alteration of the surgical instrument using the calibration device.

BRIEF DESCRIPTION OF THE DRAWINGS

The above-mentioned and other features of the disclosure, and the manner of attaining them, will become more apparent and will be better understood by reference to the following description of embodiments of the disclosure taken in conjunction with the accompanying drawings, wherein:

FIG. 1 is a perspective view of an exemplary milling instrument;

FIG. 2 is another perspective view of the exemplary milling instrument of FIG. 1, further illustrating a burr;

FIG. 5 is a top view of a guide for use with the exemplary milling instrument of FIG. 2;

FIGS. 7A-7C are perspective views of various exemplary burrs.

Corresponding reference characters indicate corresponding parts throughout the several views. The exemplifications set out herein illustrate embodiments of the disclosure and such exemplifications are not to be construed as limiting the scope of the invention in any manner.

DETAILED DESCRIPTION

Figure 3:
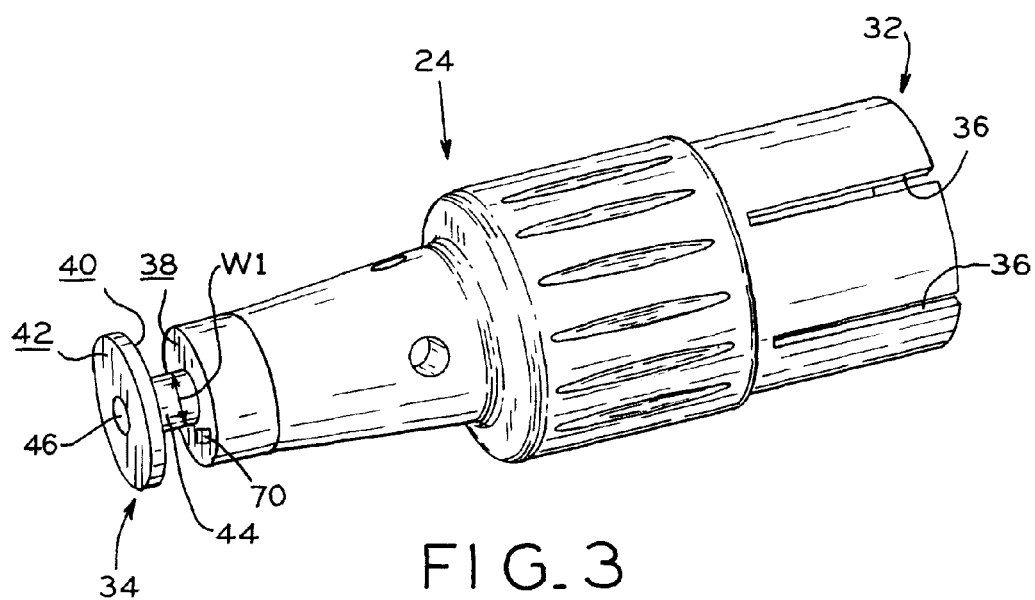
FIG. 3 is a perspective view of a burr guard of the exemplary milling instrument of FIG. 1.

Referring now to FIG. 1, an exemplary milling instrument system 20 is shown and generally may include handpiece 22 and guard 24. Handpiece 22 may be any rotary or oscillatory instrument which provides rotation or oscillation for cutting, drilling, or reaming bone or other tissue, such as a burr or an oscillating saw blade, for example, attached thereto. In an exemplary embodiment, the rotation device attached to handpiece 22 is burr 26, as shown in FIG. 2. Handpiece 22 may include proximal end 28 and distal end 30. As described herein, the term "proximal" refers to the end of an instrument closest to a user during use and the term "distal" refers to the end of an instrument furthest away from a user during use. In an exemplary embodiment, handpiece 22 is a Brasseler Handpiece, for example, Model No. PM-M10-200, available from Brasseler USA™, of Savannah, Ga.

Guard 24 may be removably attached to handpiece 22 and may be secured thereto via any suitable method, such as a snap-fit connection, welding, pinning, or a press-fit connection, for example. Guard 24 may provide support for burr 26. In an exemplary embodiment, guard 24 may be a disposable component of system 20. Guard 24 may include proximal end 32 and distal end 34. Proximal end 32 may include a plurality of slots 36 that facilitate attachment of guard 24 to handpiece 22. In particular, slots 36 expand to allow proximal end 32 to be slightly deformed such that guard 24 easily slides over a portion (hidden by guard 24 in FIG. 1) of distal end 30 of handpiece 22 for attachment therewith.

Referring to FIG. 2, system 20 may include burr 26 or an alteration device attached to handpiece 22. Burr 26 may include cutting or alteration portion 25 with a plurality of cutting edges 29 (FIG. 4) and shaft 27 extending proximally through throughbore 46 of guard 24 and connected to handpiece 22 such that rotary or oscillatory motion may be transmitted to burr 26 from handpiece 22. In an exemplary embodiment, guard 24 is positioned between handpiece 22 and cutting portion 25 and interface 48 may define a transition from handpiece 22 to guard 24. Burr 26 also includes distal end 50 which may define a distal-most dimension of alteration by burr 26. Burr 26 defines a longitudinal distance between distal end 50 and proximal end 53 of shaft 27. Proximal end 53 of shaft 27 abuts handpiece 22 at interface 54, as described below, when burr 26 is fully inserted into handpiece 22.

Figure 4:
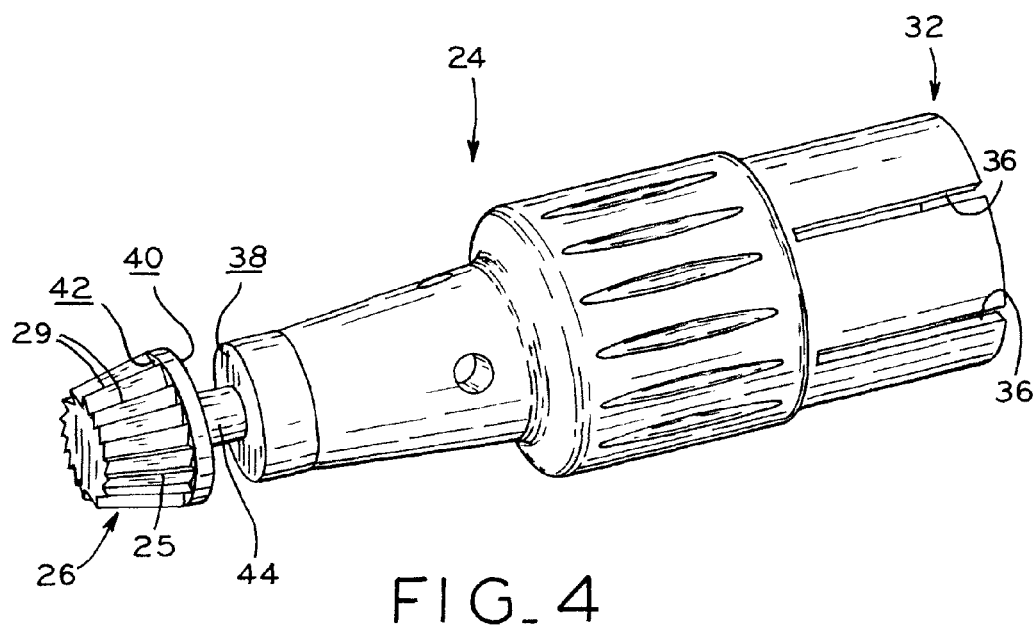
FIG. 4 is a perspective view of the burr guard of FIG. 3, further illustrating a burr.

As shown in FIGS. 2-4, distal end 34 of guard 24 includes first surface 38, second surface 40, surface 42, and intermediate portion 44. Throughbore 46 of guard 24 may extend through intermediate portion 44. First surface 38, second surface 40, and intermediate portion 44 may be used in conjunction with guide 60 (FIG. 5) having track 62 in which intermediate portion 44 engages during movement of handpiece 22 to provide guidance for handpiece 22. Intermediate portion 44 may have a width dimension W1 substantially matching a width dimension W2 of track 62 such that first surface 38 and second surface 40 are prevented from axial translation with respect to guide 60, i.e., the widths of first surface 38 and second surface 40 are greater than width W2 of track 62.

In an alternative embodiment, a user of system 20 may know the location of first surface 38 via use of a computer assisted surgery (CAS) system. The CAS system may track the location of first surface 38, such as with at least one marker 70 attached to surface 38 during movement of handpiece 22 such that the user may accurately use system 20 to remove a predetermined amount of bone or other tissue. Marker 70 may be trackable in an optical-based tracking system, a radiofrequency-based tracking system, an infrared-based tracking system, or any other suitable tracking system.

Referring now to FIGS. 1 and 2, the abutment between proximal end 53 of shaft 27 and handpiece 22 at abutment surface 52 defines interface 54. In an exemplary embodiment, interface 54 defines an interlocking engagement between shaft 27 and handpiece 22 such as to facilitate transmittal of rotational motion from handpiece 22 to shaft 27. The distance between interface 54 and first surface 38 of guard 24 may define dimension A. For any exemplary guard 24, dimension A may be known or otherwise provided to a user of system 20 because guard 24 is attached to handpiece 22 in the same manner and position regardless of a longitudinal length of guard 24.

Referring again to FIG. 2, first surface 38 of guard 24 and distal end 50 of burr 26 define dimension B. Dimension B provides a repeatable and predictable depth of alteration with burr 26. When used with a guide, first surface 38 may engage surface 64 (FIG. 5) of guide 60 and intermediate portion 44 of guard 24 may follow track 62 provided in guide 60. During a surgical procedure, dimension A may be a known value based on which guard 24 is used. Also, the longitudinal length between distal end 50 and proximal end 53 of burr 26 is known or otherwise provided to a user. Dimension B may be defined as the difference between dimension A and the length of burr 26. A user of system 20 may predefine dimension B by choosing an appropriately sized burr 26 and guard 24. Dimension B provides a predictable and repeatable depth of alteration with cutting portion 25 of burr 26.

Guard 24 may be formed of a polymeric material in an exemplary embodiment. In alternative embodiments, guard 24 may be formed of metallic materials or combinations of polymeric and metallic materials.

In operation and referring to FIG. 2, system 20 is assembled by attaching guard 24 to handpiece 22 in any suitable manner, as described above. Burr 26 is then attached to handpiece 22 by sliding shaft 27 through throughbore 46 and into locking engagement with handpiece 22. To use system 20, handpiece 22 is grasped by a surgeon and a rotation or oscillation is imparted through handpiece 22 to burr 26. Guide 60 (FIG. 5) may be attached directly or proximate to an anatomical structure to be altered. Guide 60 may include track 62 which defines an alteration pattern and surface 64 which sets a depth of distal end 50 of burr 26, i.e., first surface 38 of guard 24 abuts surface 64 of guide 60 such that the predetermined depth or reach of burr 26 is defined by the abutment between first surface 38 and surface 64. Guard 24 may engage guide 60 (FIG. 5), e.g., via engagement between track 62 and intermediate portion 44, and dimension B provides a repeatable and predictable depth of alteration to the anatomical structure. In an alternative embodiment, guide 60 may be vertically adjusted relative to the anatomical structure to which guide 60 is attached to vary the possible depth of alteration with burr 26.

Figure 6A:
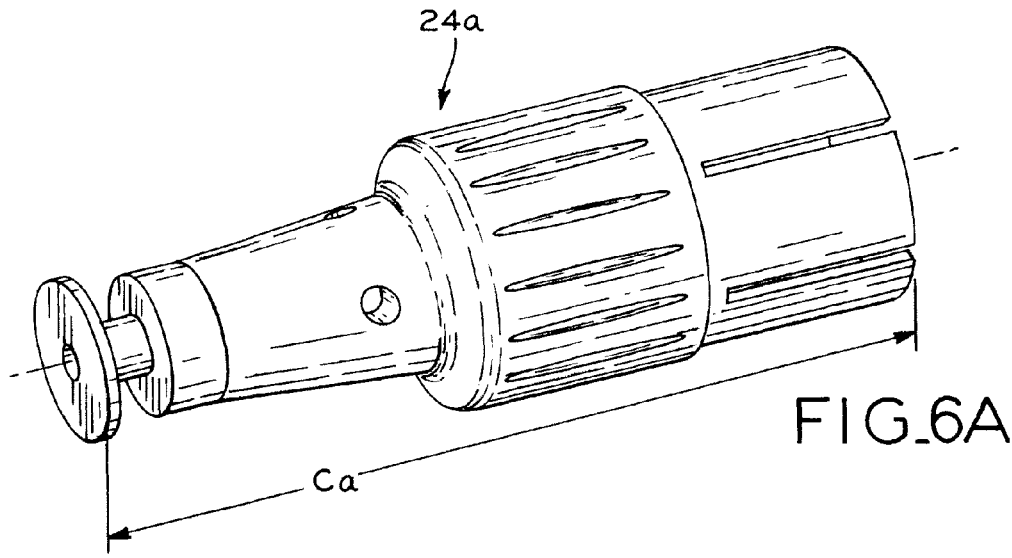
FIGS. 6A-6C are perspective views of various exemplary burr guards.
Figure 6B:
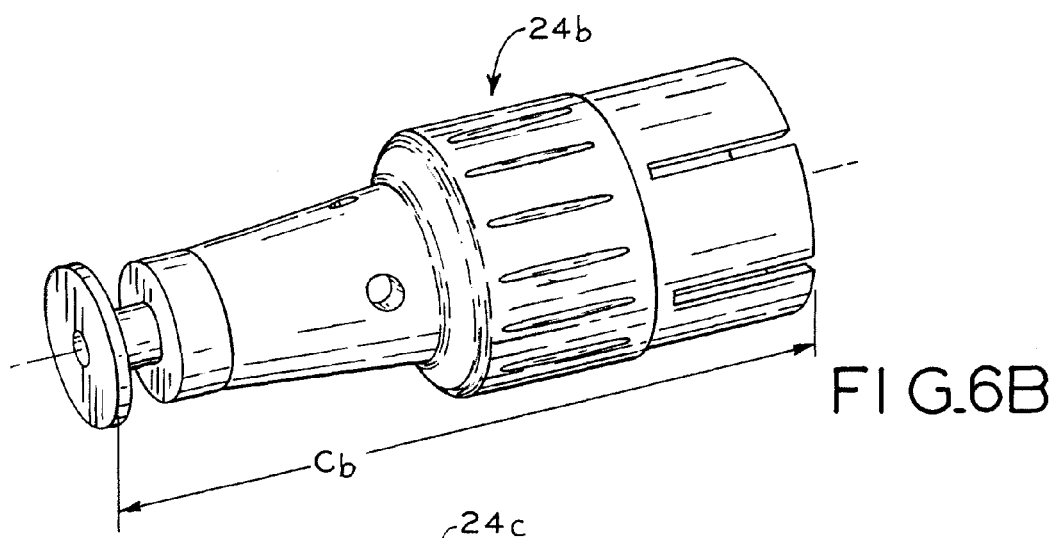
Figure 6C:
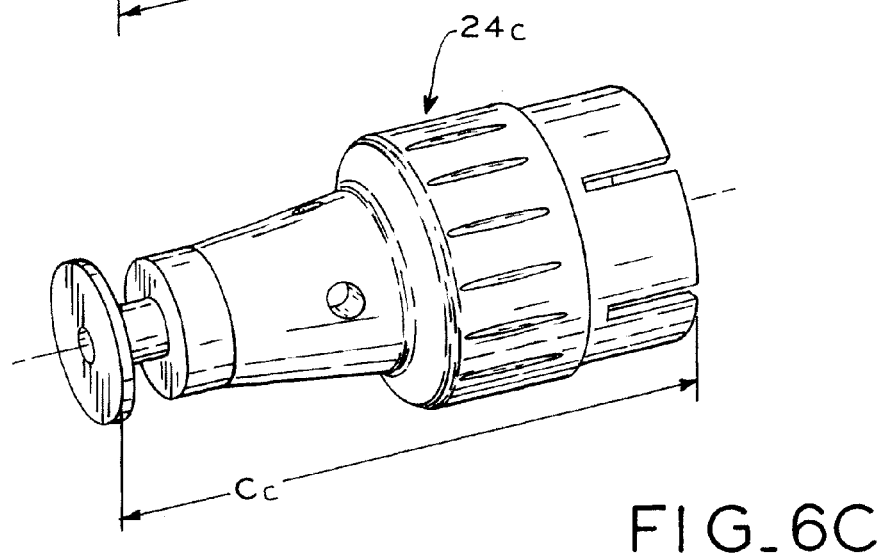

Referring now to FIGS. 6A-6C and 7A-7C, system 20 may include a plurality of burrs 26 and guards 24 which may define varying dimensions A and B. As shown in FIGS. 6A-6C, system 20 may include a plurality of guards 24a, 24b, 24c which define overall longitudinal dimensions Ca, Cb, Cc. Each dimension Ca, Cb, Cc corresponds to a different dimension A which may be selected by a surgeon during or prior to a surgical procedure. For example, dimension A for guard 24a is larger than dimension A for guard 24b, and dimension A for guard 24b is larger than dimension A for guard 24c. Also, as shown in FIGS. 7A-7C, system 20 may include a plurality of burrs 26a, 26b, 26c which define different longitudinal lengths Da, Db, Dc between distal end 50 and proximal end 53. For example, assuming guard 24 remains the same, burr 26a defines a larger dimension B than burr 26b, and burr 26b defines a larger dimension B than burr 26c. Such a system may allow a user of system 20 to selectively choose a combination of burr 26 and guard 24 which provides a desired dimension B. A surgeon may also select a burr 26 depending on other factors such as the desired speed of burr 26 and/or the material being altered, for example, by selecting a burr 26 to sculpt or shape a bone or other tissue, or, alternatively, by selecting a burr 26 to remove bone or tissue.

In one embodiment, system 20 may be used with a computer assisted surgery (CAS) system, such as the system described in co-pending U.S. patent application Ser. No. 11/610,728, entitled AN IMAGELESS ROBOTIZED DEVICE AND METHOD FOR SURGICAL TOOL GUIDANCE, assigned to the assignee of the present application, the disclosure of which is hereby expressly incorporated herein by reference. For example, handpiece 22 may be affixed to a robotic arm and the CAS system may provide a virtual guide structure to guide resection of an anatomical structure to a predetermined depth set by dimension B.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A system for use in resecting tissue of an anatomical structure, the system comprising:
    a surgical instrument;
    a plurality of cutting devices selectively attachable to said surgical instrument and configured to resect the tissue, each said cutting device defining a first longitudinal dimension, said first longitudinal dimension of each of said plurality of cutting devices being different from one another; and
    a plurality of calibration devices selectively attachable to said surgical instrument, each said calibration device defining a second longitudinal dimension, said second longitudinal dimension of each of said plurality of calibration devices being different from one another,
    wherein each of said plurality of cutting devices is configured to cooperate with each of said plurality of calibration devices to set a depth of resection for said surgical instrument, said depth of resection for any combination of one of said plurality of cutting devices and one of said plurality of calibration devices being substantially equal to the difference between said first longitudinal dimension of said one of said plurality of cutting devices and said second longitudinal dimension of said one of said plurality of calibration devices, whereby said depth of resection is adjustable by altering the combination of said one of said plurality of cutting devices and said one of said plurality of calibration devices,
    wherein each of said plurality of calibration devices includes a reference surface and said surgical instrument includes a receptacle for selectively housing said plurality of cutting devices, said receptacle defining a proximal end, said second longitudinal dimension of each of said plurality of calibration devices defined between said proximal end of said receptacle and said reference surface of each of said plurality of calibration devices when each of said plurality of calibration devices is attached to said surgical instrument.

2. The system of claim 1, wherein each of said plurality of cutting devices includes a cutting portion and a shaft, each of said shafts extendable into and attachable to said surgical instrument, each of said shafts including a proximal end and each of said cutting portions including a distal end, wherein said first longitudinal dimension of each of said plurality of cutting devices is defined between said proximal end of each of said shafts and said distal end of each of said cutting portions.

3. The system of claim 1, wherein at least one of said plurality of calibration devices includes a guidance structure for mating engagement with a guide attached to the tissue.

4. The system of claim 1, wherein at least one of said plurality of calibration devices includes a tracking element for use with a computer assisted surgery system.

5. The system of claim 2, wherein each of said plurality of calibration devices includes a throughbore for selectively receiving each of said shafts of said plurality of cutting devices.

6. The system of claim 1, wherein each of said plurality of calibration devices includes a proximal end attachable to said surgical instrument and having a plurality of expandable fingers, wherein said plurality of expandable fingers are configured to expand when said proximal end of each of said plurality of calibration devices is attached to said surgical instrument.

7. The system of claim 1, wherein said surgical instrument selectively drives said plurality of cutting devices.

8. The system of claim 3, wherein said guidance structure of said at least one of said plurality of calibration devices includes a second surface opposing said reference surface, and an intermediate portion extending therebetween, said intermediate portion being received by the guide when said guidance structure is in mating engagement with the guide.

9. The system of claim 8, wherein said reference surface is positioned adjacent to a top surface of the guide and said second surface is positioned adjacent to a bottom surface of the guide when said guidance structure is in mating engagement with the guide.

* * * * *